(12) United States Patent
Hirohara et al.

(10) Patent No.: US 6,354,705 B1
(45) Date of Patent: Mar. 12, 2002

(54) ANTERIOR SEGMENT PHOTOGRAPHING APPARATUS FOR PRODUCING IMAGES OF A SECTION OF THE ANTERIOR SEGMENT OF THE EYE TO BE EXAMINED BY USING SLIT LIGHT BEAM

(75) Inventors: Yoko Hirohara; Toshifumi Mihashi, both of Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 0 days.

(21) Appl. No.: 09/419,612

(22) Filed: Oct. 18, 1999

(30) Foreign Application Priority Data

Oct. 23, 1998 (JP) .............................................. 10-302654

(51) Int. Cl.$^7$ ................................................. A61B 3/10

(52) U.S. Cl. ...................................................... 351/214

(58) Field of Search ................................. 351/205, 206, 351/208, 209, 210, 211, 214, 220, 221

(56) References Cited

U.S. PATENT DOCUMENTS 5,002,384 A * 3/1991 Trachtman .................... 351/203
5,423,798 A * 6/1995 Crow ............................. 606/4

* cited by examiner

Primary Examiner—George Manuel
(74) Attorney, Agent, or Firm—Oblon, Spivak, McClelland, Maier & Neustadt, P.C.

(57) ABSTRACT

An anterior segment photographing apparatus comprises a slit light beam projecting system for projecting a slit light beam on an eye to be examined, an image forming optical system disposed right in front of the eye to be examined and capable of forming an image of a section of the anterior segment of the eye represented by the slit light beam reflected from the eye on a light receiving, a concave mirror having a concave reflecting surface in a shape of rotational symmetry with respect to the optical axis of the image forming optical system and capable of collecting and reflecting the reflected slit light beam reflected from the eye, and a reflecting mirror for reflecting the reflected light reflected from the concave mirror toward the image forming optical system.

4 Claims, 7 Drawing Sheets

ANTERIOR SEGMENT PHOTOGRAPHING APPARATUS FOR PRODUCING IMAGES OF A SECTION OF THE ANTERIOR SEGMENT OF THE EYE TO BE EXAMINED BY USING SLIT LIGHT BEAM

BACKGROUND OF THE INVENTION

1. Field of the Invention

The present invention relates to an anterior segment photographing apparatus for producing images of sections of the anterior segment of an eye to be examined by projecting a slit light beam on the eye.

2. Description of the Related Art

A known anterior segment photographing apparatus for photographing the sections of the anterior segment of the eye to be examined produces images of sections of the anterior segment by illuminating the anterior segment including a cornea and a crystalline lens with a slit light beam, projecting the slit light beam from the front of the eye to be examined along the lens axis thereof, and receiving images of sections of the anterior segment thus illuminated from a direction oblique to the lens axis thereof.

The anterior segment photographing apparatus of this kind sections the anterior segment by planes including meridians around the lens axis of the eye to be examined, and photographs images of sections of the anterior segment. The anterior segment photographing apparatus in a related art is provided with a photographing optical system having an optical axis inclined at a predetermined angle to the lens axis of the eye to be examined in which the photographing optical system is turned around the lens axis of the eye.

Since the photographing optical system of this anterior segment photographing apparatus of the related art is disposed with its optical axis inclined at the predetermined angle to the lens axis of the eye to be examined, a space must be secured for the turning of the photographing optical system around the lens axis of the eye, besides a large rotative driving mechanism is necessary to let the photographing optical system revolve, and accordingly the anterior segment photographing apparatus is necessarily large.

Since the rotative driving mechanism is large, the photographing optical system can be revolved only at low revolving speeds, so that much time is necessary for obtaining an image of a section of the anterior segment in each plane including a meridian.

SUMMARY OF THE INVENTION

Accordingly, it is an object of the present invention to provide an anterior segment photographing apparatus having small construction and capable of obtaining an image of a section of the anterior segment in each plane including a meridian in a short time.

According to a first aspect of the present invention, an anterior segment photographing apparatus comprises a slit light beam projecting system for projecting a slit light beam on an eye to be examined, an image forming optical system disposed right in front of the eye capable of forming an image of a section of the anterior segment of the eye represented by the slit light beam reflected from the eye on a light receiving surface, a concave mirror having a concave reflecting surface in a shape of rotational symmetry with respect to the optical axis of the image forming optical system capable of collecting and reflecting the slit light beam reflected from the eye, and a reflecting mirror for reflecting the light reflected from the concave mirror toward the image forming optical system.

Accordingly, the anterior segment photographing apparatus can be formed small in construction and is capable of quickly producing an image of a section of the anterior segment in a plane including a meridian.

According to a second aspect of the present invention, in the anterior segment photographing apparatus, the slit light beam can be turned around the optical axis of the slit light beam projecting system, and the image forming optical system and the reflecting mirror are turned around the optical axis of the image forming optical system according to the turn of the slit light beam.

According to a third aspect of the present invention, in the anterior segment photographing apparatus, the reflecting mirror has a cylindrical reflecting surface.

According to a fourth aspect of the present invention, in the anterior segment photographing apparatus, the concave mirror forms an image of a section of the anterior segment of the eye to be examined on a first image surface, and the image forming optical system forms the image of the section of the anterior segment formed on the first image surface on the light receiving surface.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

An anterior segment photographing apparatus in a preferred embodiment according to the present invention will be described with reference to the accompanying drawings.

Figure 1:
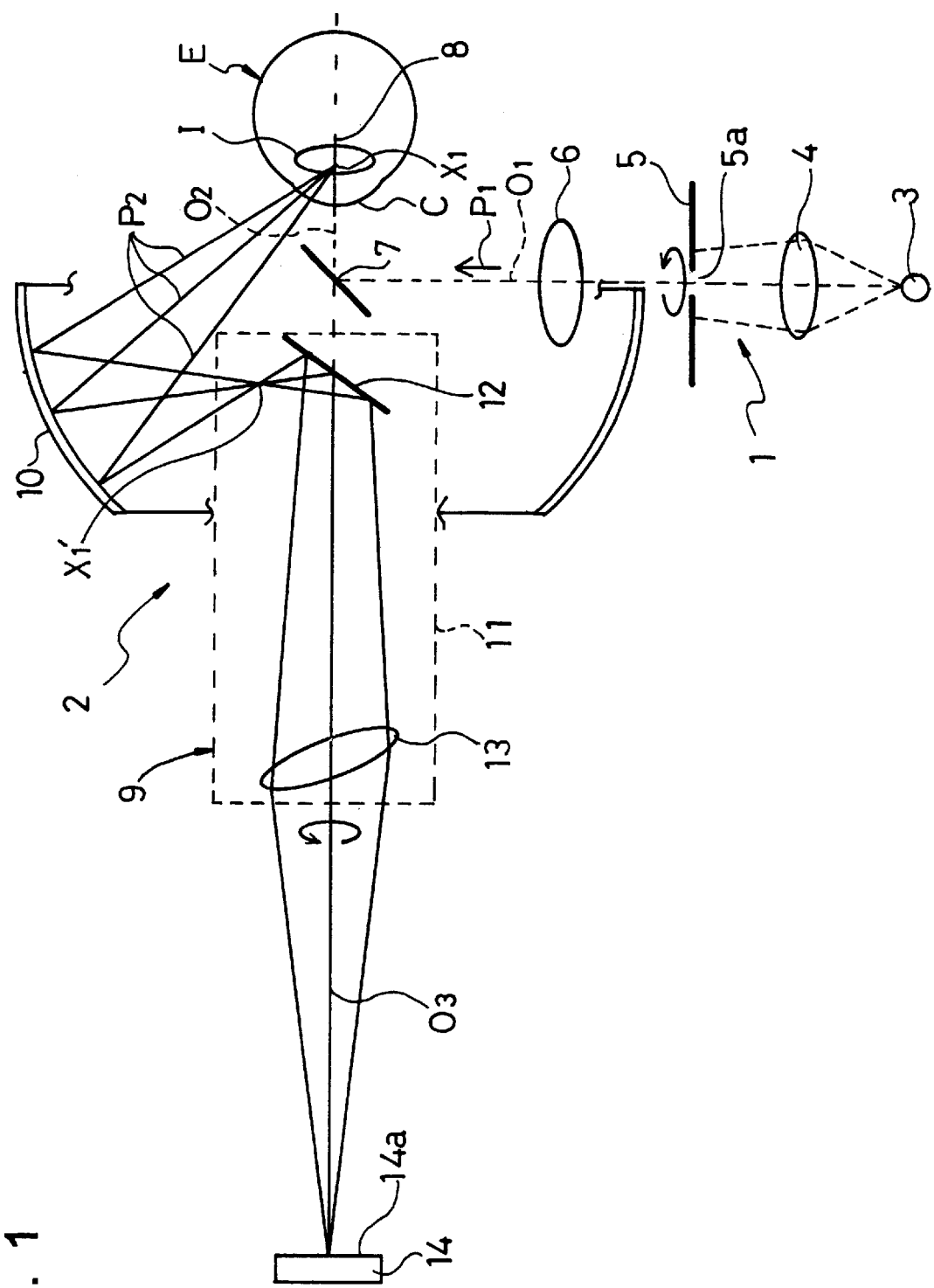
FIG. 1 is a diagrammatic view of an entire optical system of an anterior segment photographing apparatus in a preferred embodiment according to the present invention.
Figure 2:
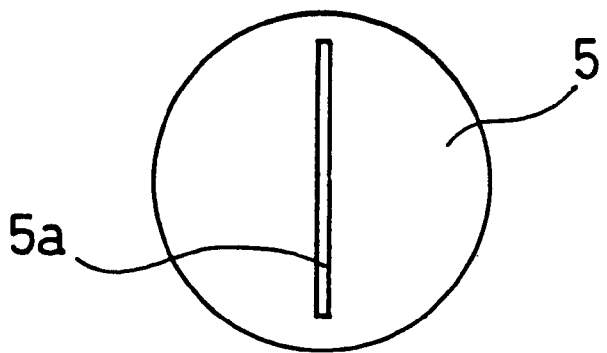
FIG. 2 is a plan view of a slit plate shown in FIG. 1.

Referring to FIG. 1, there are shown an eye E to be examined, a slit light beam projecting system 1 and a photographing optical system 2. The slit light beam projecting system 1 comprises an illuminating light source 3, a condenser lens 4, a slit plate 5, a projection lens 6 and a reflecting mirror 7. As shown in FIG. 2, the slit plate 5 is provided with a slit 5a. The optical axis O1 of the slit light beam projecting system 1 is perpendicular to the optical axis O2 of the eye E. The reflecting mirror 7 is inclined at 45° to the optical axis O2 of the eye.

Figure 3:
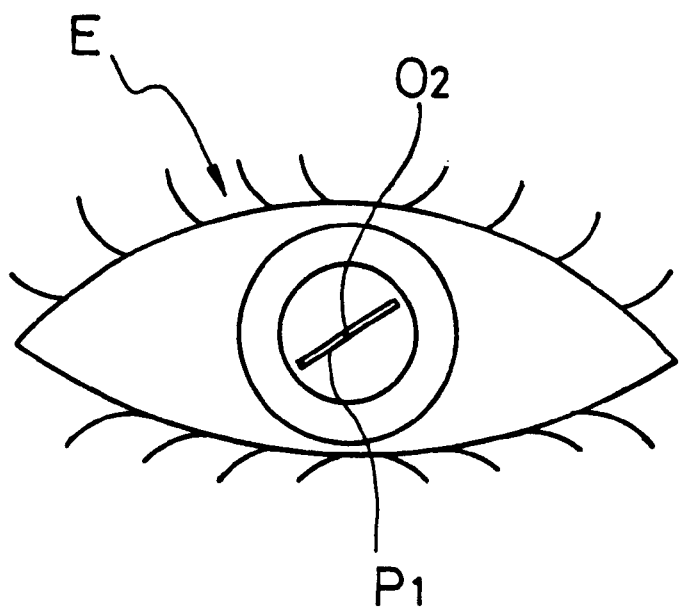
FIG. 3 is a pictorial view of assistance in explaining a slit light beam projected on the anterior segment of an eye to be examined.

In a state shown in FIG. 1, the slit 5a extends perpendicularly to the plane of FIG. 1. Illuminating light rays emitted by the illuminating light source 3 are gathered by the condenser lens 4 and led to the slit plate 5, then the gathered light rays are converted into a thin, flat slit light beam P1 through the slit 5a. The slit light beam P1 travels through the projection lens 6 and falls on the reflecting mirror 7. The slit plate 5 is turned around according to the turn of an image forming optical system, which will be described later. Thus, the slit light beam P1 is turned about the optical axis O2 of the eye E as shown in FIG. 3.

The slit light beam P1 reflected by the reflecting mirror 7 enters the eye E, traveling through the cornea C and the crystalline lens I of the eye E into the interior of the eye E. The slit light beam P1 is turned to section the anterior segment in each plane including a meridian. A slit image 8 is formed on the eye E by the slit light beam P1 projected through the projection lens 6 as shown in FIG. 1. The anterior segment represented by the slit image 8 is photographed as an image of a section thereof.

The photographing optical system 2 has an image forming optical system 9 and a concave reflecting mirror 10. The image forming optical system 9 has a lens barrel 11. A reflecting mirror 12 and an image forming lens 13 are held by the lens barrel 11. The image forming optical system 9 is disposed right in front of the eye E with the optical axis O3 thereof in alignment with the optical axis O2 of the eye E. The optical axis O3 of the image forming optical system 9 is defined as a line which passes the respective centers of the image forming lens 13 and a CCD 14, which will be described later.

Figure 4:
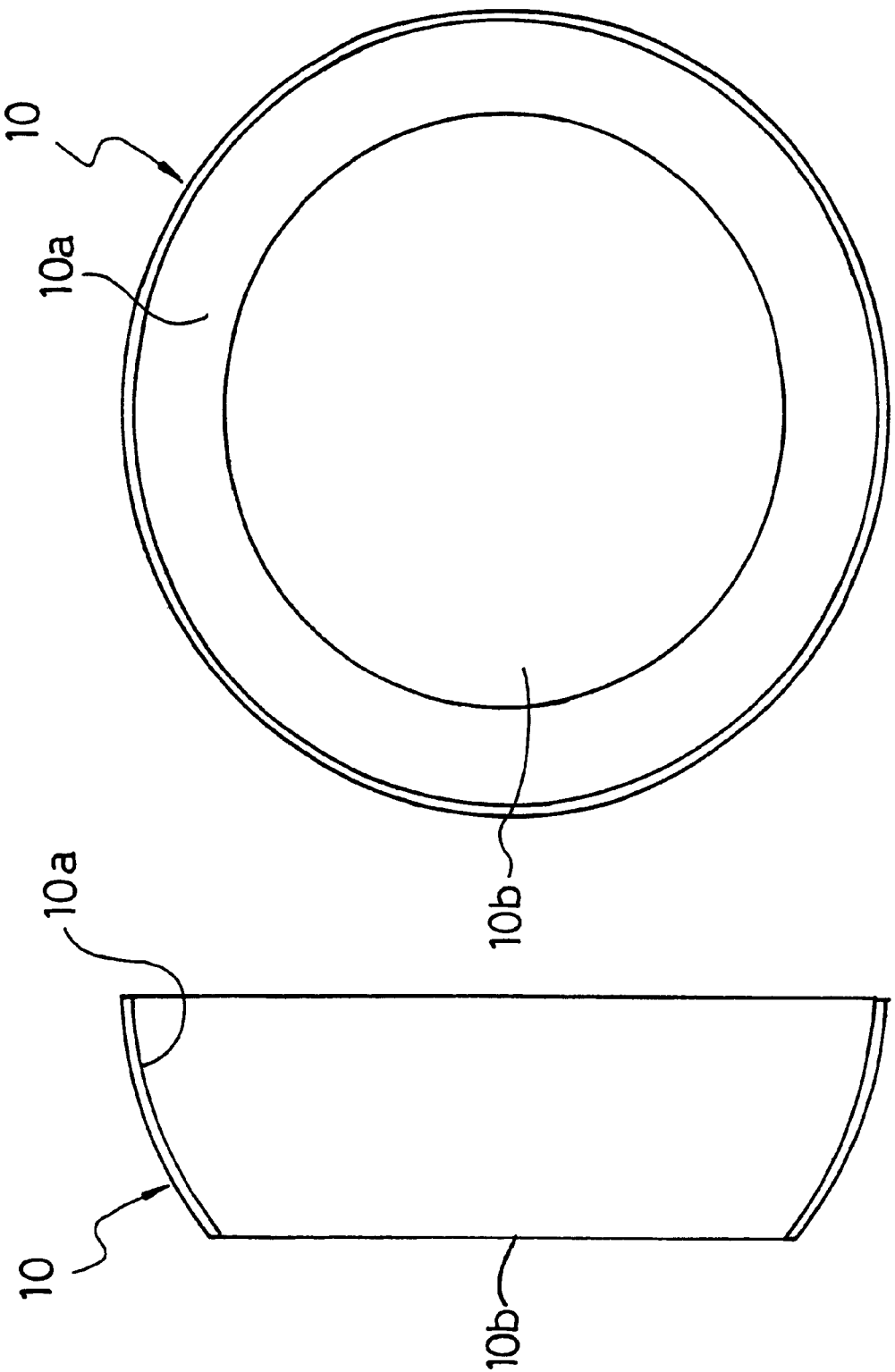
FIG. 4(a) is a sectional view of a concave reflecting mirror shown in FIG. 1 in a meridional plane.
FIG. 4(b) is a plan view of the concave reflecting mirror as viewed from where the eye to be examined presents.

Referring to FIGS. 4(a) and 4(b), a concave reflecting mirror 10 has a concave reflecting surface 10a having a shape of rotational symmetry with respect to the optical axis O3 of the image forming optical system 2, and a central opening 10b. The curvature of the concave reflecting surface 10a on a meridional plane shown in FIG. 1 and that of the same on a sagittal plane are different from each other. The concave reflecting mirror 10 collects and reflects scattered, reflected light rays P2 from the eye E. The shape of the concave reflecting surface 10a in a meridional plane may be either spherical or aspherical, taking aberration correction into account.

Figure 5:
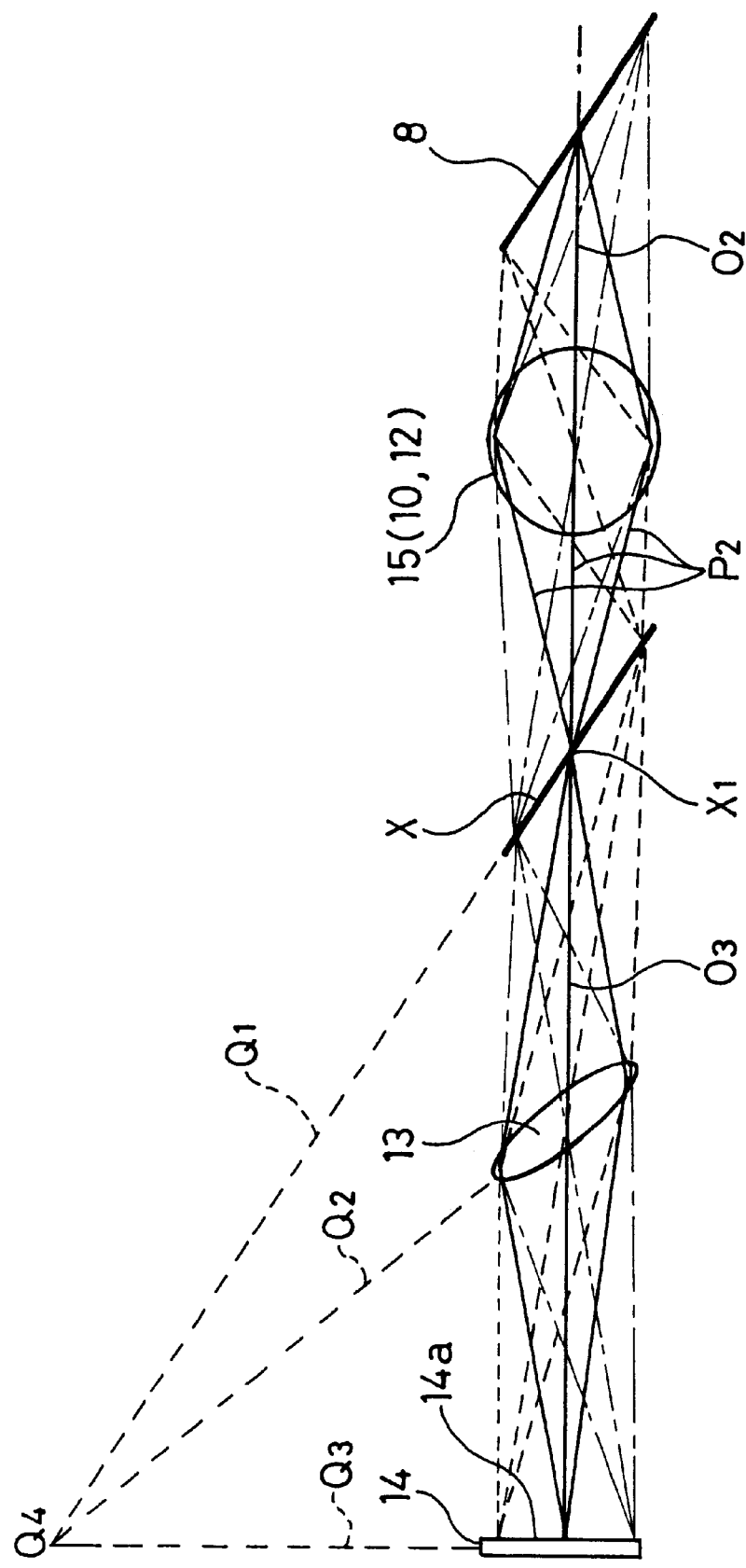
FIG. 5 is a typical view of optical systems shown in FIG. 1, illustrating the positional relation between an image of a section of the anterior segment, a reflecting system, an image forming lens and a CCD.

The lens barrel 11 is inserted through the central opening 10b into the concave reflecting mirror 10. The scattered, reflected light rays P2 collected and reflected by the concave reflecting surface 10a are converged on a first image surface X in a meridional plane. Consequently, an image of the section of the anterior segment in the meridional plane is formed on the first image surface X (refer to FIG. 5). FIG. 1 shows a state in which the scattered, reflected light rays P2 reflected from a point X1 in the meridional plane are converged on a point X1'.

The scattered, reflected light rays P2 converged in the meridional plane are reflected toward the image forming lens 13 by the reflecting mirror 12. The scattered, reflected light rays P2 then travel through the image forming lens 13 and incident on the light receiving surface 14a of the CCD 14.

The image forming lens 13 is disposed so as to be inclined to the optical axis O3. As typically shown in FIG. 5, the principal light rays among the scattered, reflected light rays P2 fallen on the concave reflecting mirror 10 are inclined to the image 8 of the section of the anterior segment. A reflecting system 15 including the concave reflecting mirror 10 and the reflecting mirror 12, the image forming lens 13 and the CCD-14 are disposed so that a prolongation Q1 extending from the first image surface X on which the scattered, reflected light rays P2 are formed into an image, a prolongation Q2 extending perpendicular to the optical axis of the image forming lens 13, and a prolongation Q3 extending perpendicular to the optical axis Q3 of the light receiving surface of the CCD 14 meet at a single point Q4. This arrangement of the components of the optical system is a known arrangement called Scheimpflug law.

A well focused image of the section of the anterior segment can be formed on the entire CCD 14, even if the slit image 8 is inclined to the optical axis O3 of the image forming optical system 9, i.e., even if the image of the section of the anterior segment is inclined.

The reflecting mirror 12 is a cylindrical mirror. The reflecting mirror 12 functions as a flat mirror in a meridional plane and as a convex mirror in a sagittal plane. Reasons for employing a cylindrical mirror as the reflecting mirror 12 will be described below.

Figure 6:
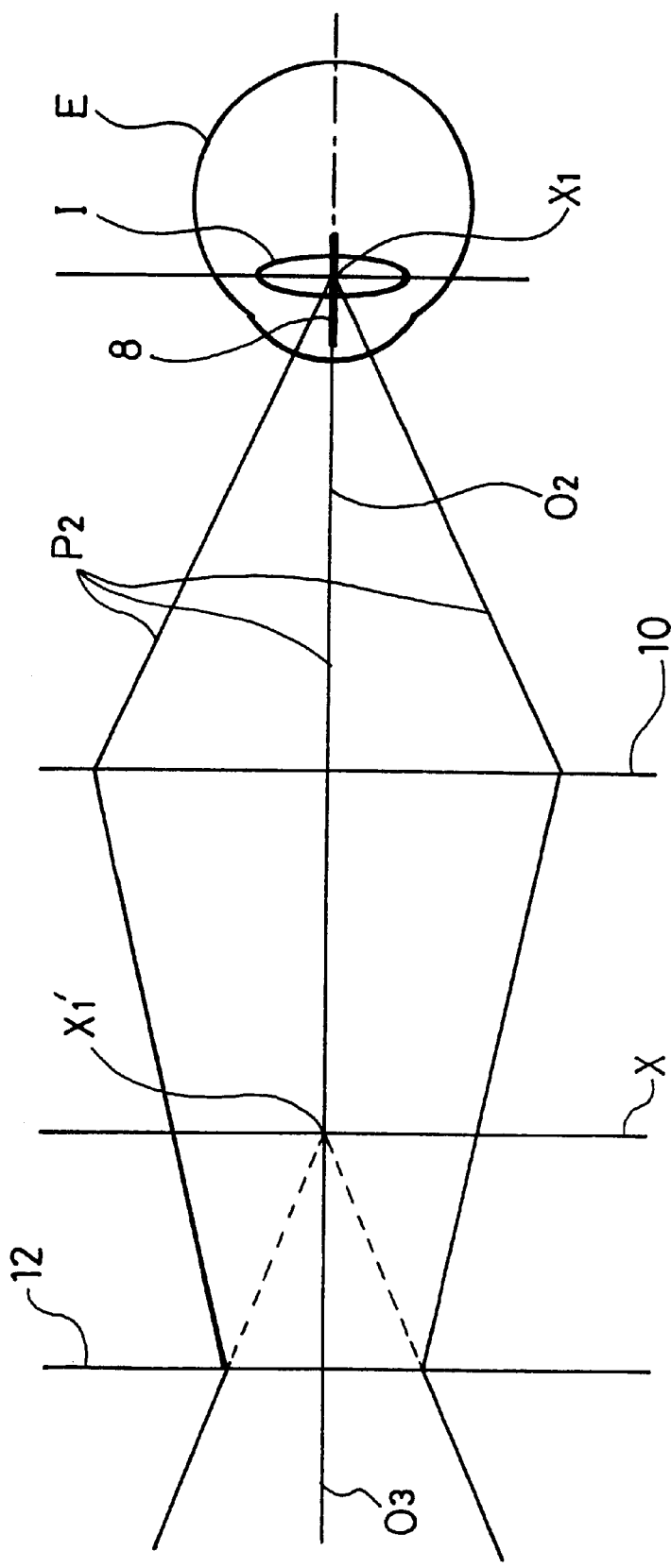
FIG. 6 is a diagrammatic view of assistance in explaining the locus of scattered, reflected light rays shown in FIG. 1 on a sagittal plane.

FIG. 6 is a diagrammatic view of assistance in explaining the scattered, reflected light rays P2 in a sagittal plane. The scattered, reflected light rays P2 from the anterior segment are converged on the point X1' by the concave reflecting surface 10a in the meridional plane because the power of the concave reflecting surface 10a is high. However, the scattered, reflected light rays P2 from the anterior segment are not converged on the single point X1' in the sagittal plane because the power of the concave reflecting surface 10a is low.

Therefore, the reflecting mirror 12, serving as a reflecting surface having cylindrical power in the sagittal plane is employed to form a virtual image on the first image surface X in the sagittal plane. The slit image 8 and the first image surface X are conjugate with respect to the reflecting system 15 in the sagittal plane. FIG. 6 typically illustrates a state in which the scattered, reflected light rays P2 emanated from the point X1 are reflected by the reflecting mirror 12, and a virtual image of the point X1 is formed at the point X1'.

Although this embodiment is provided with the reflecting mirror 12 having a cylindrical reflecting surface, a flat mirror and a cylindrical lens having power in a sagittal plane and disposed right behind the flat mirror with respect to the direction of travel of reflected light rays, a flat mirror and a cylindrical lens affixed to the flat mirror, or an anamorphic mirror having powers in a sagittal plane and a meridional plane may be used instead of the reflecting mirror 12.

Figure 7:
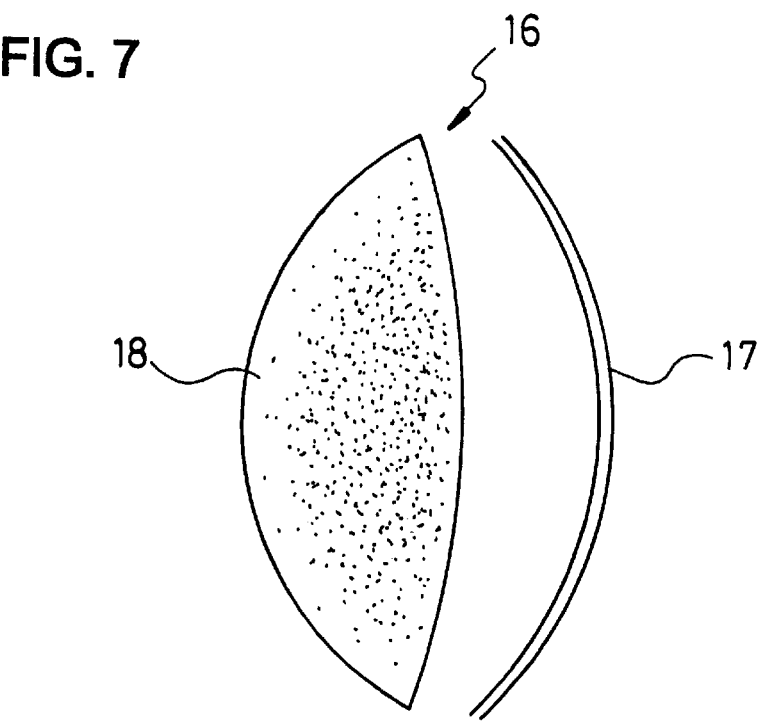
FIG. 7 is a view of an example of an image of a section of the anterior segment.
Figure 9:
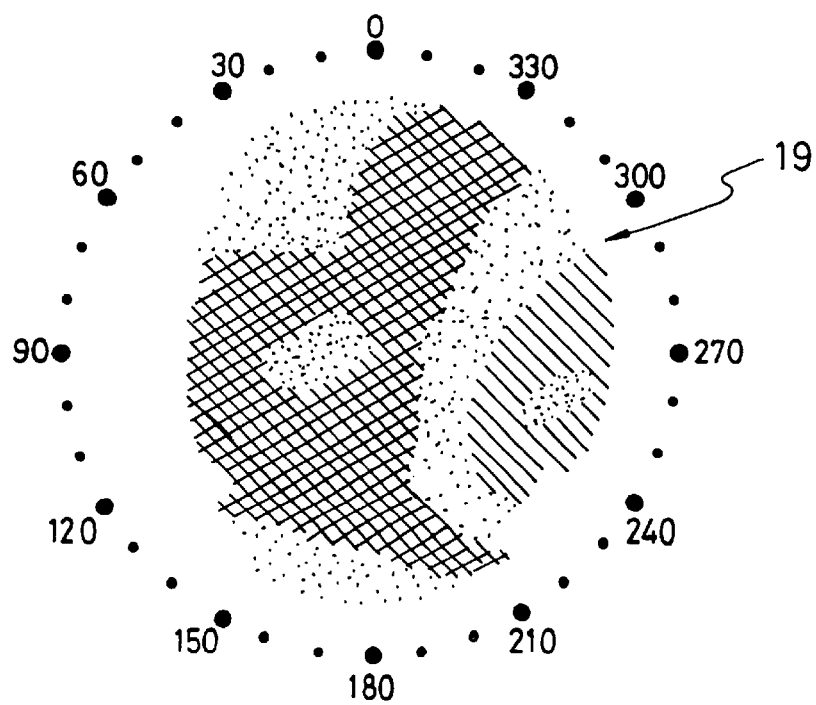
FIG. 9 is a pictorial view of an example of the cornea in a three-dimensional shape.
Figure 8:
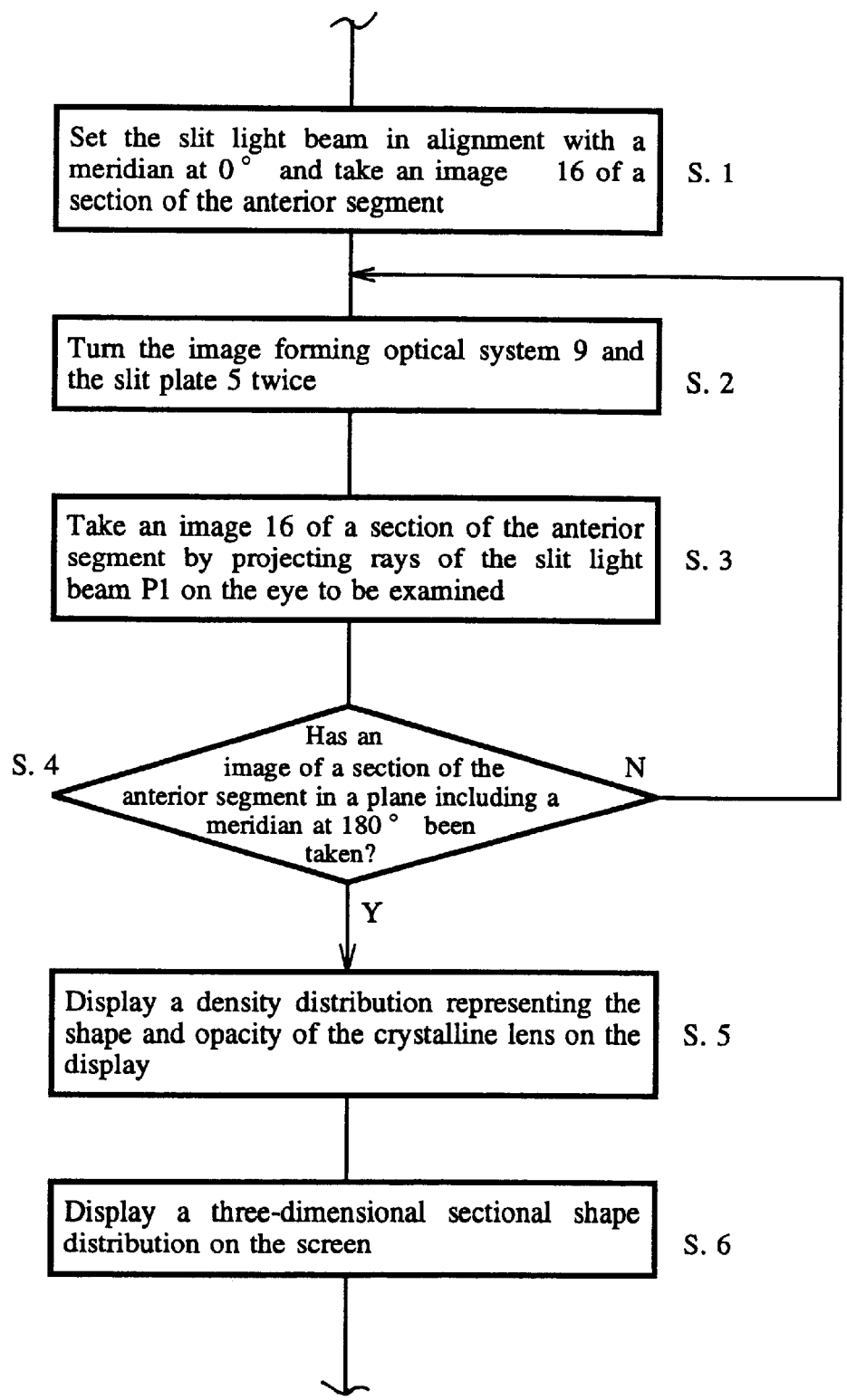
FIG. 8 is a flowchart for briefly explaining an example of a photographing procedure to be carried out by the anterior segment photographing apparatus according to the present invention.

The lens barrel 11 can be turned through 360° about the optical axis O3 by a rotative driving mechanism, not shown. An image 16 of a section of the anterior segment shown in FIG. 7 is photographed (refer to step S1 in FIG. 8) by setting the slit light beam P1 in alignment with a meridian at 0°. Subsequently, the image forming optical system 9 and the slit plate 5 are turned twice (refer to step S2) and the rays of the slit light beam P1 is projected to photograph an image 16 of the section of the anterior segment (refer to step S3), and steps S2 to S4 are repeated until an image 16 of a section of the anterior segment in a plane of a meridian at 180° is obtained. After the images of the sections in the planes including the meridians have been obtained, an image processing unit, not shown, displays a density distribution representing the shape and opacity of the crystalline lens 1 on a display, not shown (step S5). Then, the image processing unit calculates the curvatures of the cornea C on the meridians on the basis of the images 16 of the sections of the anterior segment and displays a three-dimensional sectional shape distribution 19 on the display, not shown (step S6).

In FIG. 7, indicated at 17 is an image of a section of the cornea C and at 18 is an image of a section of the crystalline lens I.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. An anterior segment photographing apparatus comprising:
    a slit light beam projecting system for projecting a slit light beam on an eye to be examined;
    an image forming optical system disposed right in front of the eye capable of forming an image of a section of the anterior segment of the eye to be examined represented by the slit light beam reflected from the eye on a light receiving surface;
    a concave mirror having a concave reflecting surface in a shape of rotational symmetry with respect to the optical axis of the image forming optical system and capable of collecting and reflecting the reflected slit light beam reflected from the eye; and
    a reflecting mirror for reflecting the reflected light reflected from the concave mirror toward the image forming optical system.

2. The anterior segment photographing apparatus according to claim 1, wherein the slit light beam can be turned about the optical axis of the slit light beam projecting system, and the image forming optical system and the reflecting mirror are turn about the optical axis of the image forming optical system in connection with the turn of the slit light beam.

3. The anterior segment photographing apparatus according to claim 1, wherein the reflecting mirror has a reflecting surface of a cylindrical surface.

4. The anterior segment photographing apparatus according to claim 1, wherein the concave mirror forms an image of a section of the anterior segment of the eye to be examined on a first image surface, and the image forming optical system forms the image of the section of the anterior segment formed on the first image surface on the light receiving surface.

* * * * *